United States Patent [19]

Stillian et al.

[11] Patent Number: 5,518,622
[45] Date of Patent: May 21, 1996

[54] ELECTROCHEMICAL PRETREATMENT SYSTEM FOR LIQUID SAMPLE ANALYSIS

[75] Inventors: John R. Stillian, Pleasanton; Archava Siriraks, Santa Clara, both of Calif.

[73] Assignee: Dionex Corporation, Sunnyvale, Calif.

[21] Appl. No.: 319,370

[22] Filed: Oct. 6, 1994

Related U.S. Application Data

[63] Continuation of Ser. No. 919,935, Jul. 27, 1992, abandoned, which is a continuation-in-part of Ser. No. 833,334, Feb. 10, 1992, abandoned.

[51] Int. Cl.$^6$ .................................................. B01D 15/08
[52] U.S. Cl. ......................... 210/635; 210/638; 210/656; 210/659; 210/198.2; 204/542
[58] Field of Search ........................... 204/301, 182.1, 204/182.3, 182.4, 182.5, 182.6, 518, 520, 522, 523, 542; 210/635, 638, 644, 686, 659, 748, 198.2, 243; 436/100, 150, 161, 175

[56] References Cited

U.S. PATENT DOCUMENTS

| | | | |
|---|---|---|---|
| 3,722,181 | 3/1973 | Kirkland | 210/198.2 |
| 3,795,313 | 3/1974 | Kirkland | 210/198.2 |
| 3,897,213 | 7/1975 | Stevens | 23/253 R |
| 3,920,397 | 11/1975 | Small | 23/230 R |
| 3,925,019 | 12/1975 | Small | 23/230 R |
| 3,926,559 | 12/1975 | Stevens | 23/230 R |
| 4,242,097 | 12/1980 | Rich | 210/662 |
| 4,265,634 | 5/1981 | Pohl | 23/230 R |
| 4,314,823 | 2/1982 | Rich | 210/662 |
| 4,403,039 | 9/1983 | Ban | 436/150 |
| 4,459,357 | 7/1984 | Jansen | 436/161 |
| 4,474,664 | 10/1984 | Stevens | 210/656 |
| 4,486,312 | 12/1984 | Slingsby | 210/656 |
| 4,751,004 | 6/1988 | Stevens | 210/659 |
| 4,999,098 | 3/1991 | Pohl | 204/301 |
| 5,045,204 | 9/1991 | Dasgupta | 210/635 |
| 5,248,426 | 9/1993 | Stillian | 210/635 |

OTHER PUBLICATIONS

Snyder, Introduction to Modern Liquid Chromatography John Wiley & Sons Inc. 1979, pp. 519–522.

*Primary Examiner*—Ernest G. Therkorn
*Attorney, Agent, or Firm*—Flehr, Hohbach, Test, Albritton & Herbert

[57] ABSTRACT

A system for pretreating sample streams including a concentrated matrix compound to neutralize the compound. The system includes an electrochemical membrane device in which sample flows through a sample flow channel of the device separated from a matrix ion receiving flow channel by an ion exchange membrane preferentially permeable to ions of the opposite charge to the ions to be analyzed. The ionic species in the thus-pretreated sample are directed to an analytical system such as an ion chromatograph.

9 Claims, 12 Drawing Sheets

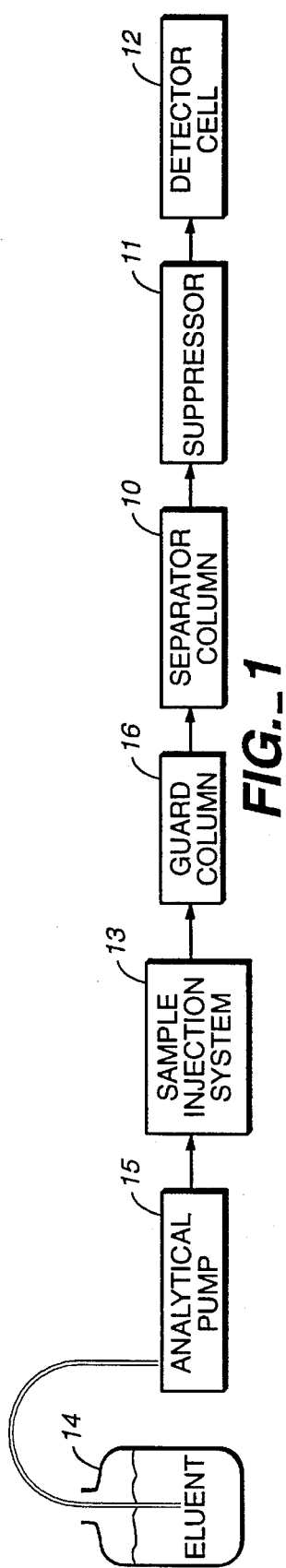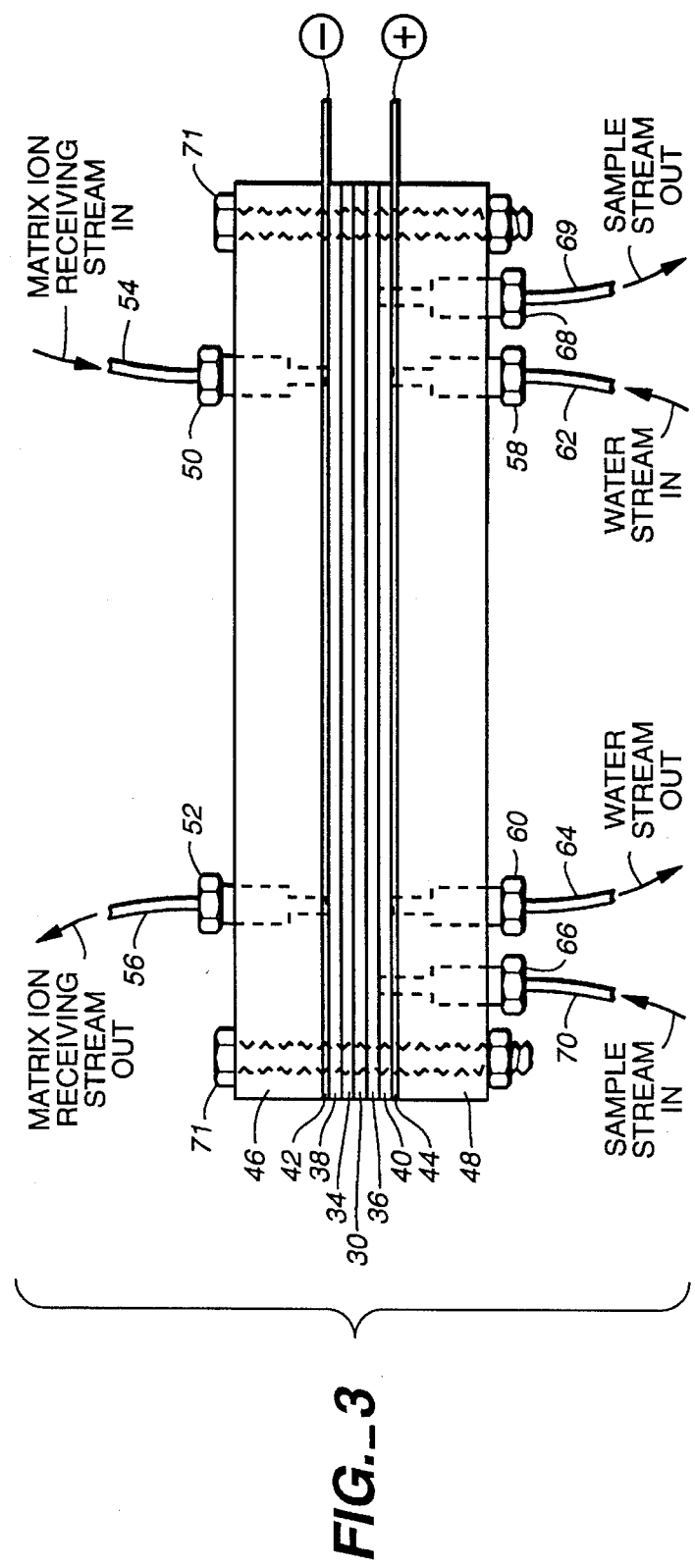

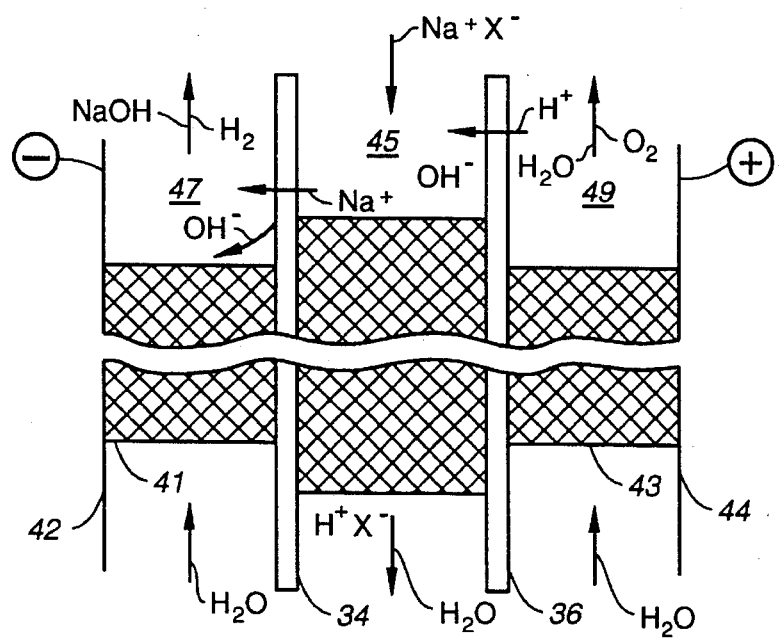
FIG._4
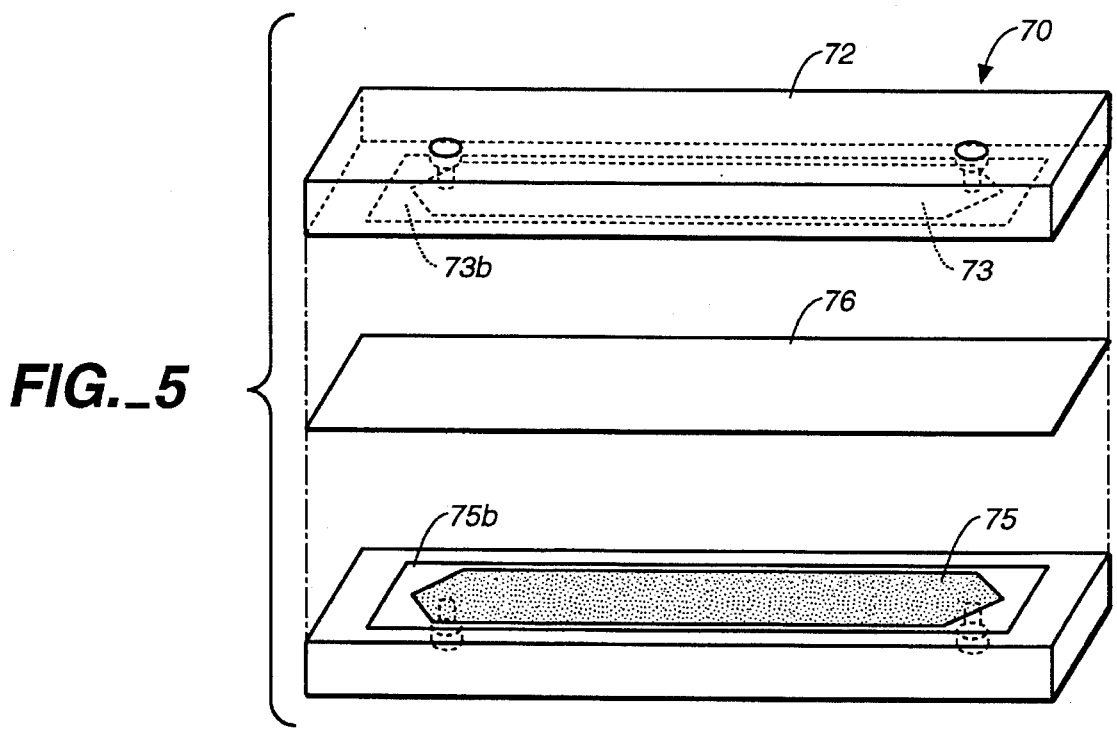
FIG._5

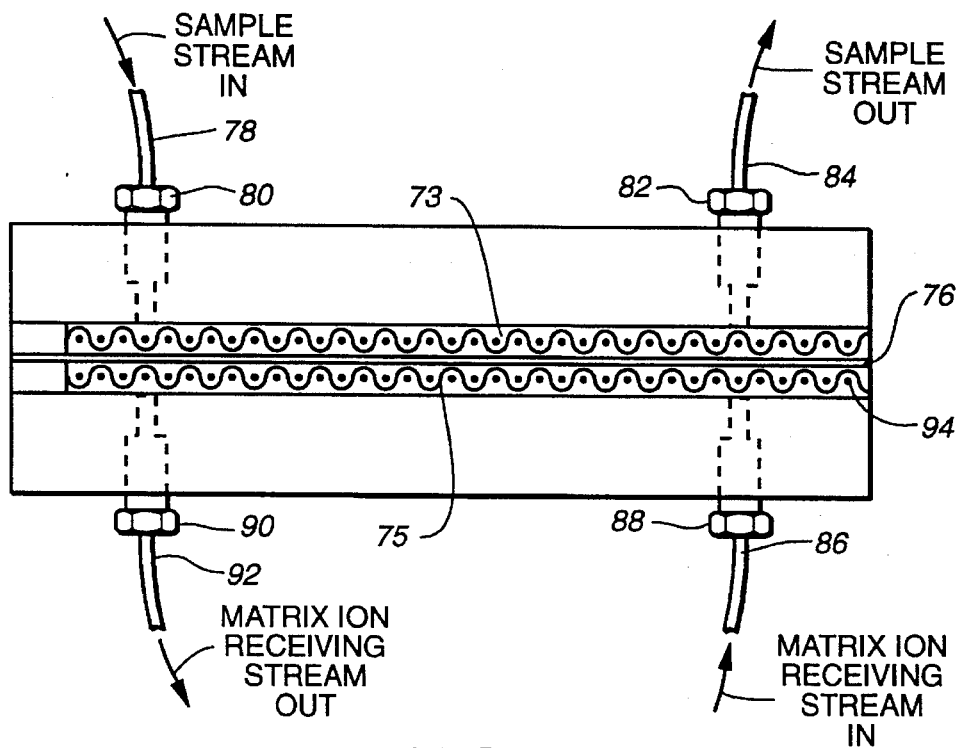
FIG._6
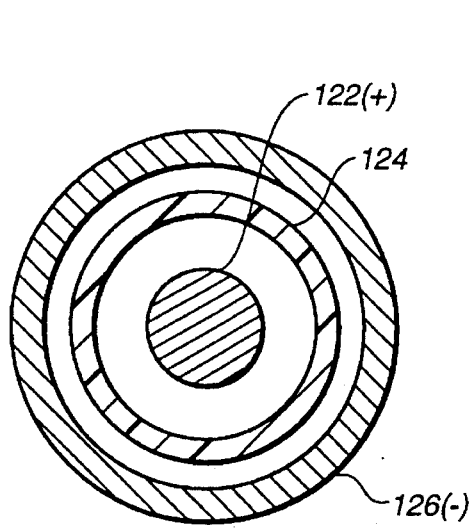
FIG._7
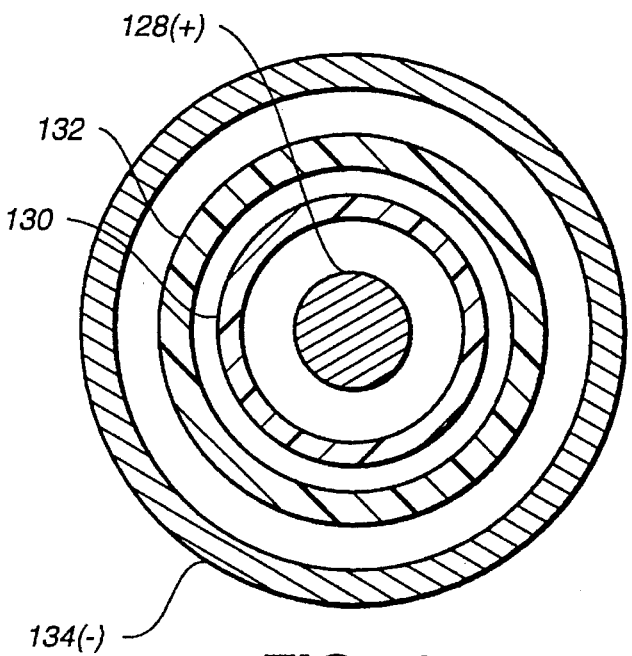
FIG._8

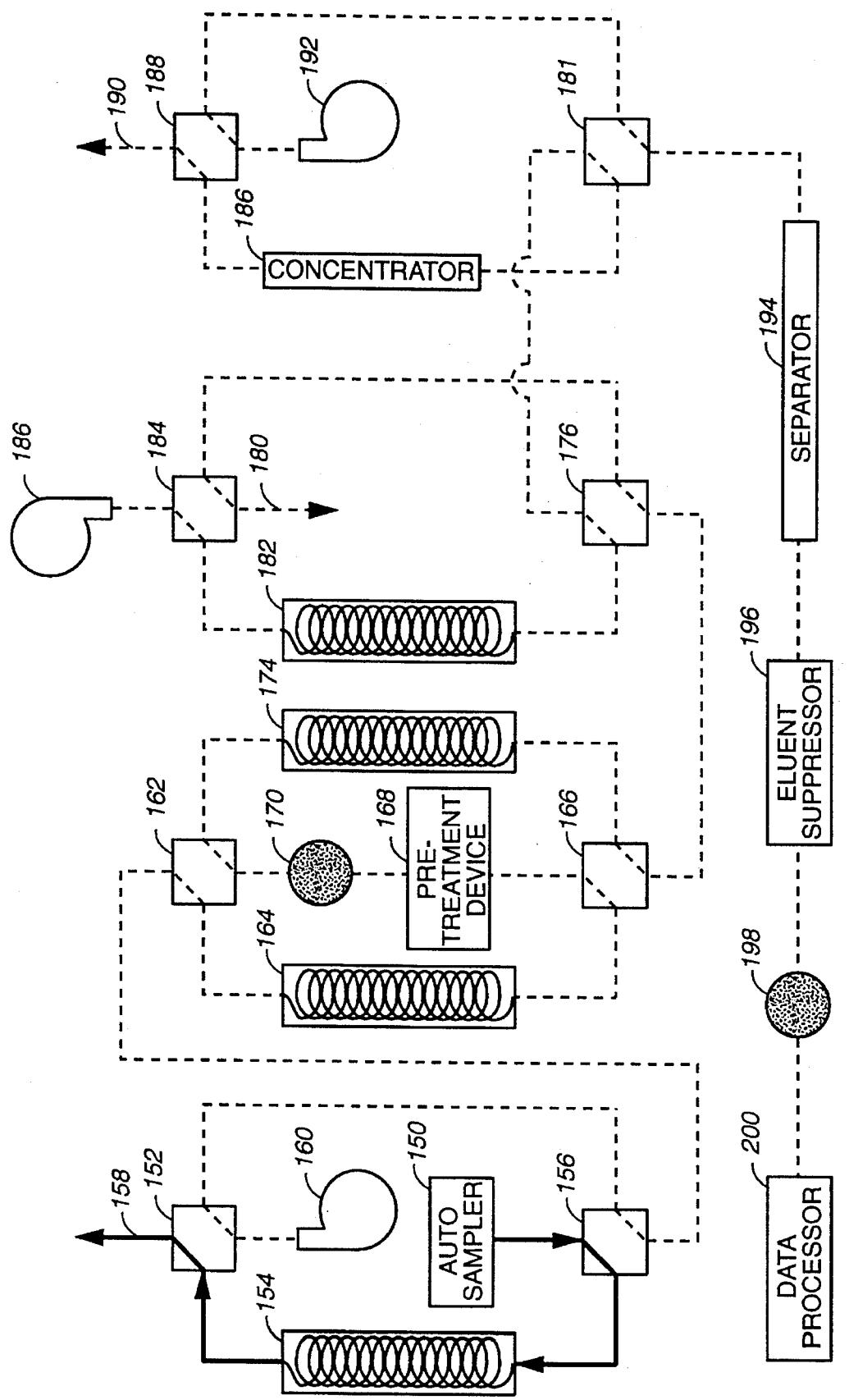
FIG._9a

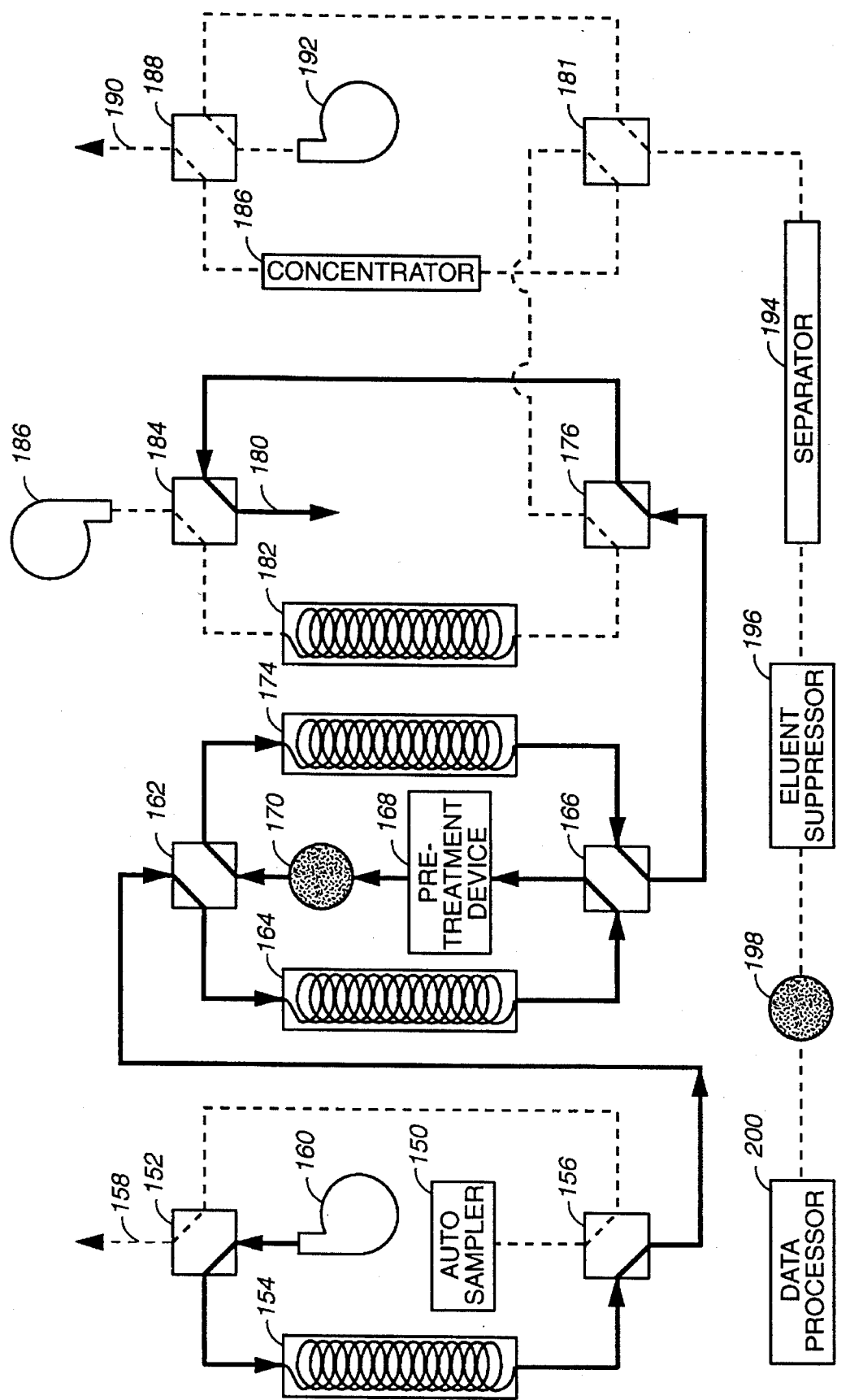
FIG._9b

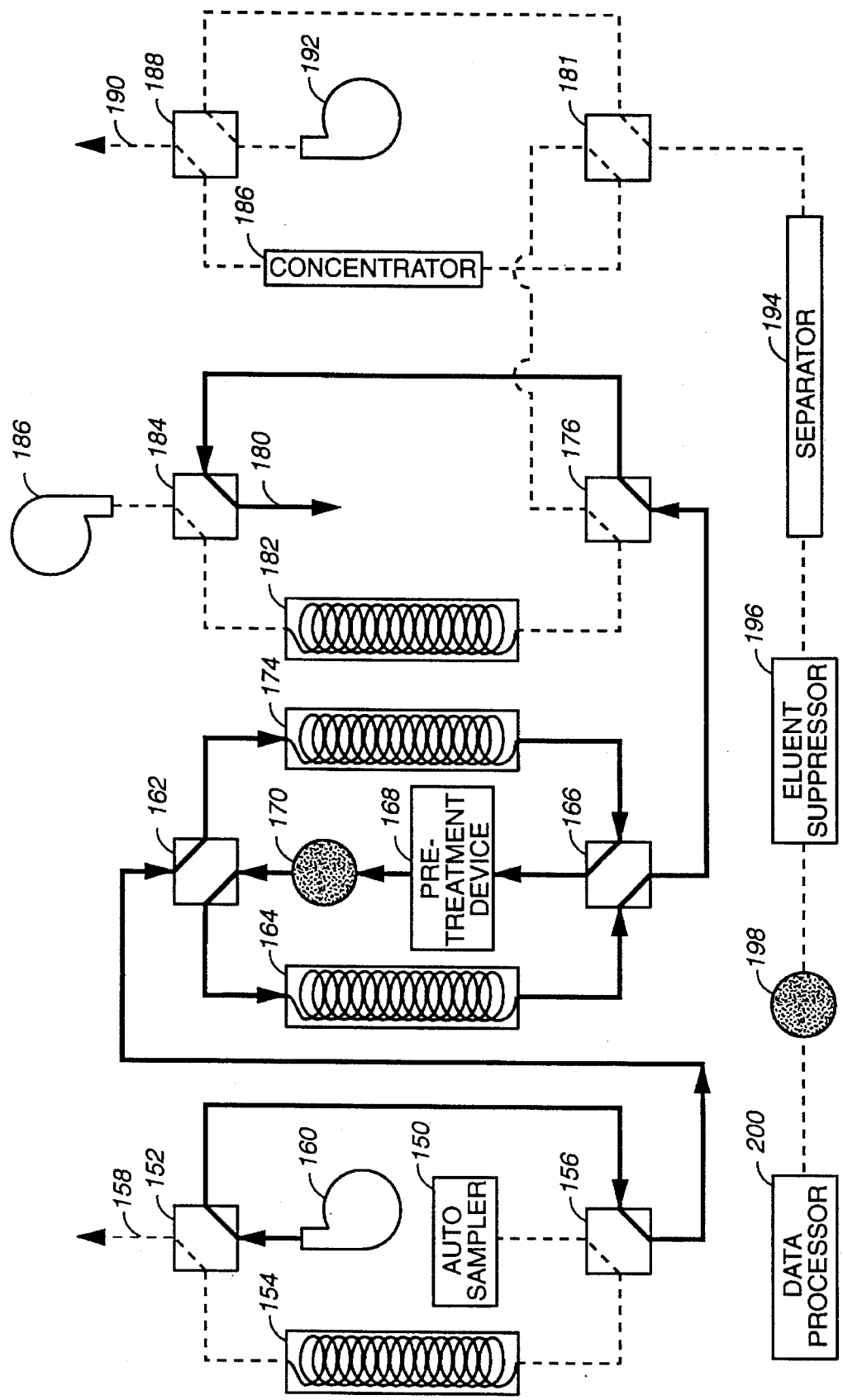
FIG._9c

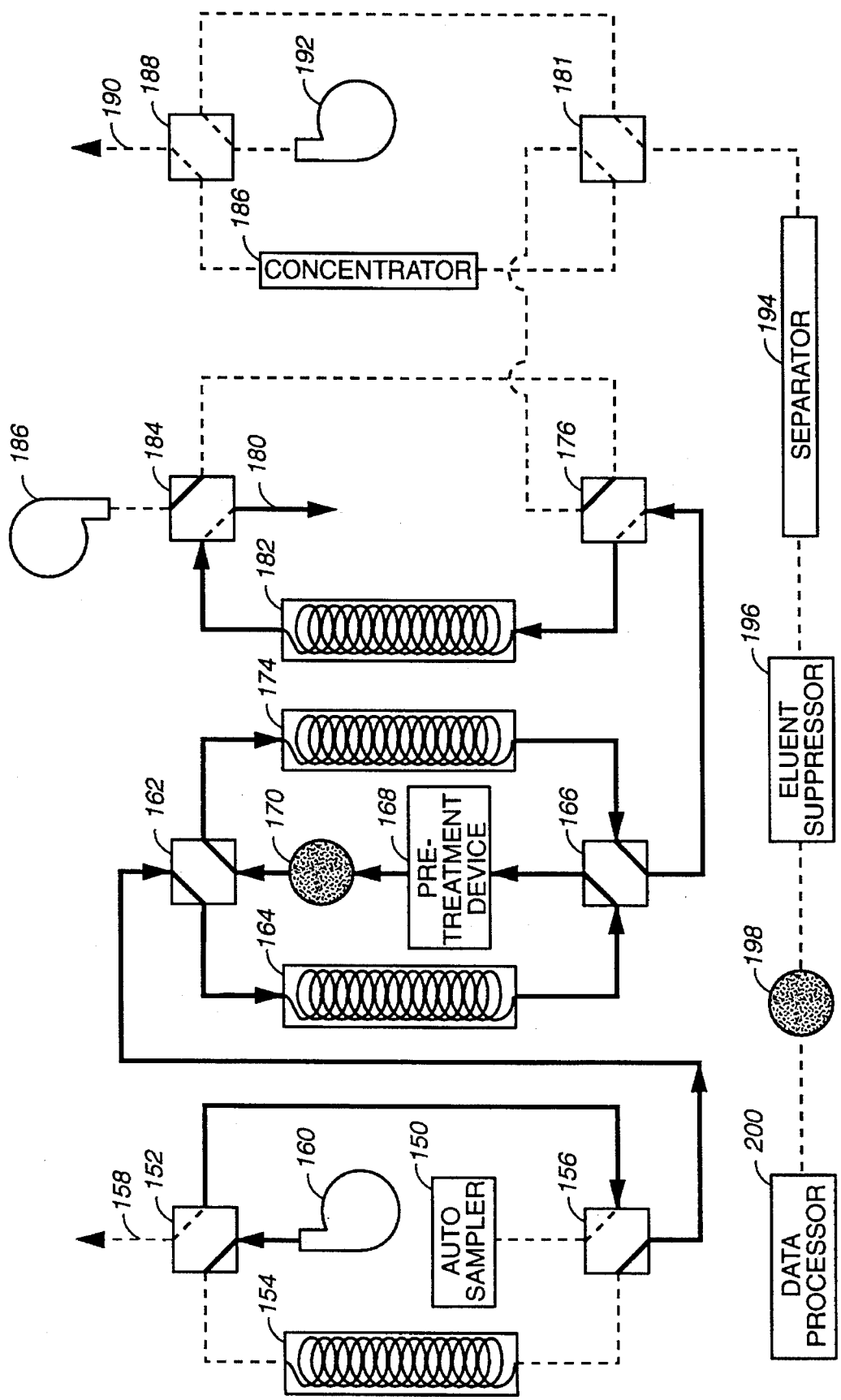
FIG._9d

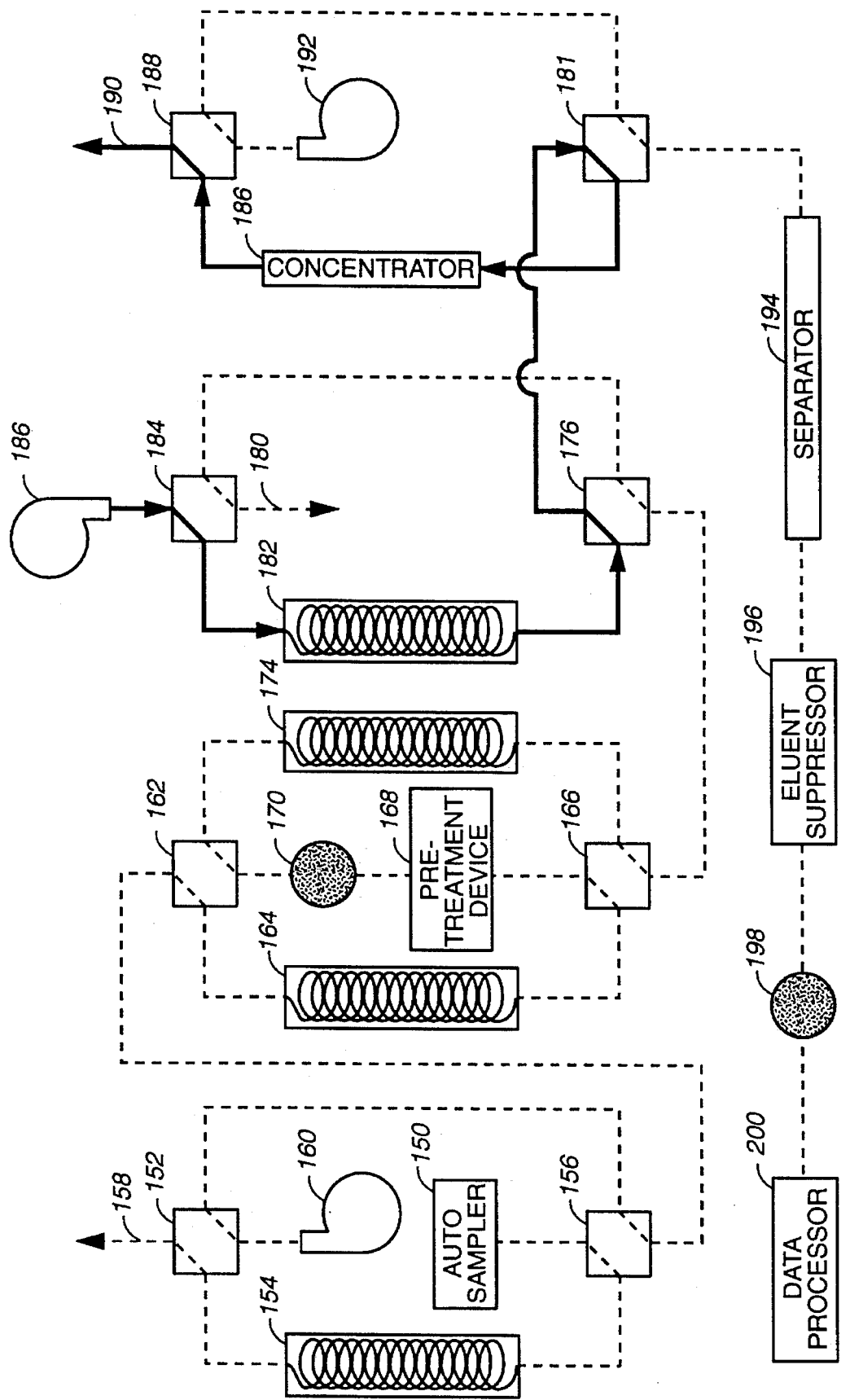
FIG._9e

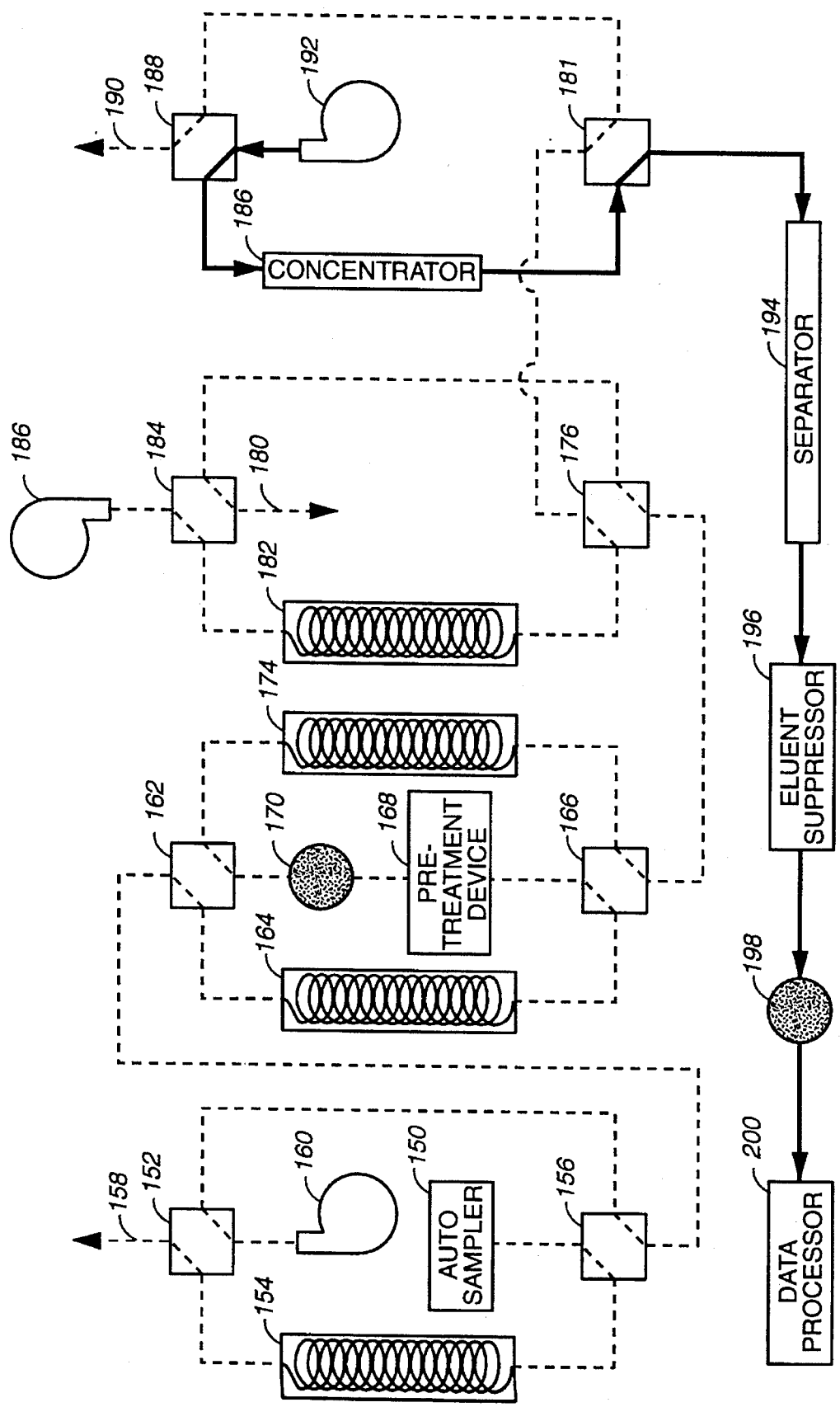
FIG._9f

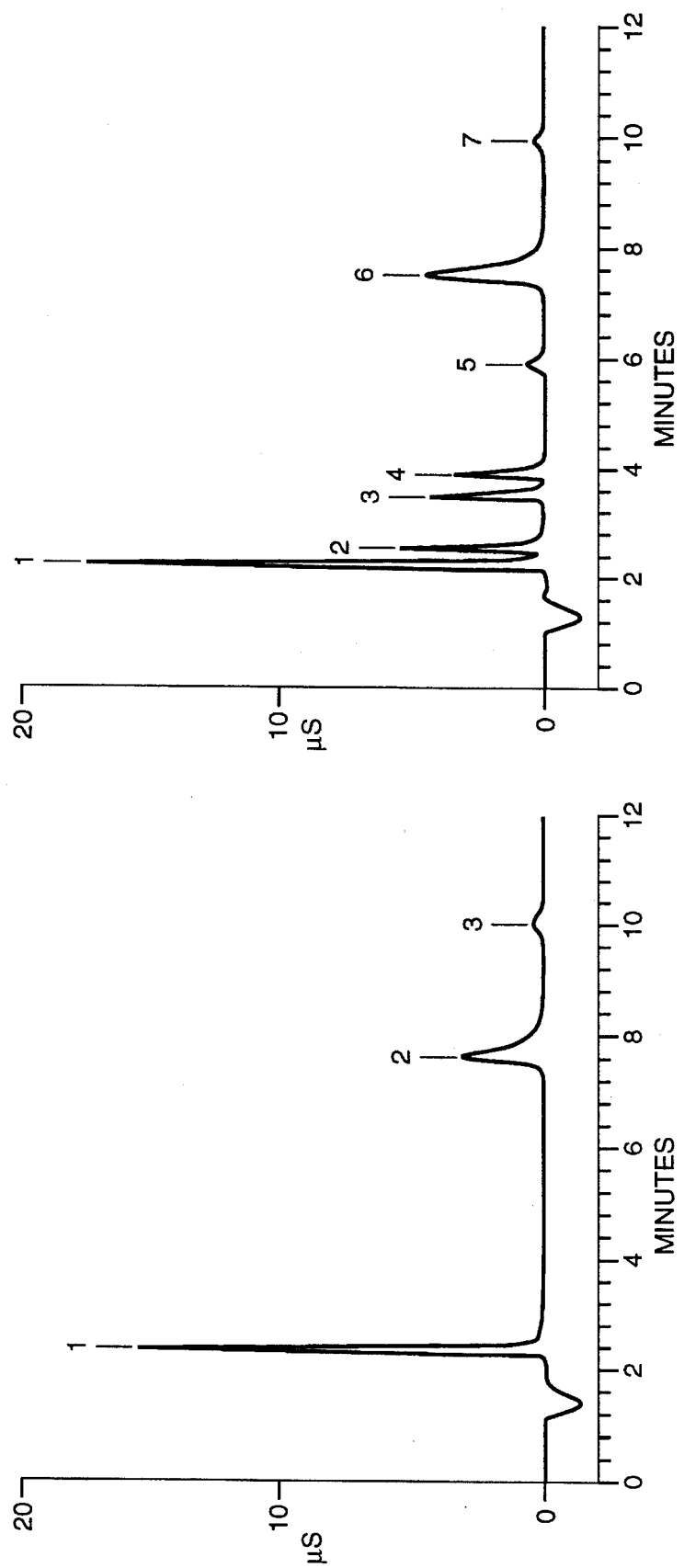
FIG._10b
FIG._10a

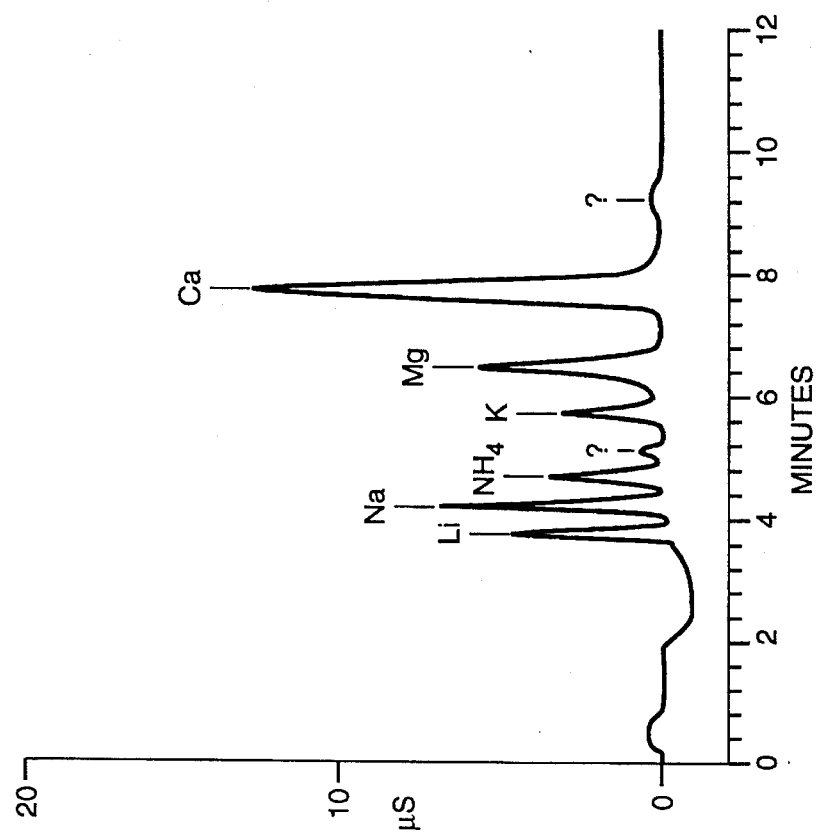
FIG._11b
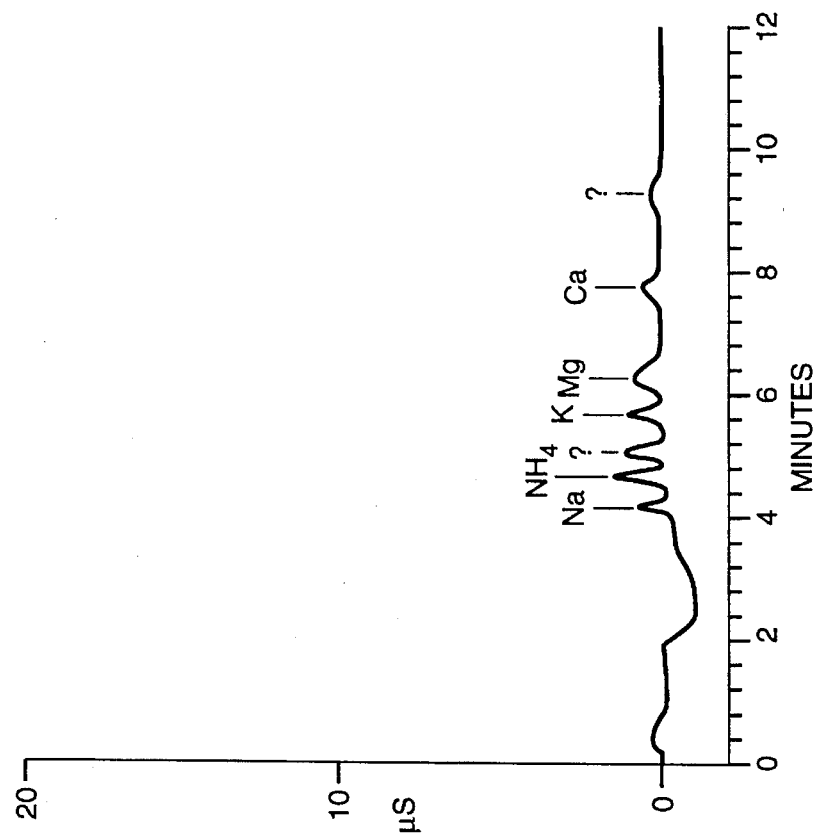
FIG._11a

5,518,622

ELECTROCHEMICAL PRETREATMENT SYSTEM FOR LIQUID SAMPLE ANALYSIS

This is a continuation, of application Ser. No. 07/919,935 filed Jul. 27, 1992, now abandoned, which, in turn, is a continuation-in-part of U.S. Ser. No. 07/833,334, filed Feb. 10, 1992, now abandoned.

BACKGROUND OF THE INVENTION

The present invention relates to a method and apparatus using electrochemical pretreatment for analysis of a liquid sample stream (e.g. by ion chromatography).

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,956,559.

Suppression or stripping of the electrolyte is described in the above prior art references by an ion exchange resin bed. A different form of suppressor column is described and published in U.S. Pat No. 4,474,664, in which a charged ion exchange membrane in the form of a fiber or sheet is used in place of the resin bed. The sample and eluent are passed on one side of the membrane with a flowing regenerant on the other side, the membrane partitioning the regenerant from the effluent of chromatographic separation. The membrane passes ions of the same charge as the exchangeable ions of the membrane to convert the electrolyte of the eluent to weakly ionized form, followed by detection of the ions.

Another form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the possibility of using water to replace the regenerant solution in the electrodialytic mode.

One problem with ion chromatography or other analytical measurements such as high performance liquid chromatography (HPLC) is for sample compounds to be detected contained in a matrix of one or more compounds of high ionic strength. For chromatography, the sample peaks are obscured by the large interfering peak of the sample matrix ion. Also, chromatography is severely changed because the sample matrix ion is of such high concentration that it becomes the major eluting ion, temporarily overriding the eluent.

A membrane suppressor device used in ion chromatography (e.g. of the type set forth in U.S. Pat. No. 4,999,098) also has been used has a pretreatment device on-line with subsequent chromatographic separation using ion chromatography. Pretreatment reduces the concentration of acid or base matrices. This technique is useful for the analysis of anions and cations only when the sample matrix is basic or acidic, respectively. This is because the suppressor device is also an ion exchange device, cation exchange for anion analysis and anion exchange for cation analysis. For example, neutralization of a basic sample matrix for analyzing anions requires the removal of the cationic co-ion to the hydroxide ion and replacing with a hydronium ion to form water for the neutralization reaction. The removal and replacement occur at an ion exchange site of the ion exchange membrane of the pretreatment device.

For some samples, continuous membrane based suppressor pretreatment device may have the required capacity to treat the matrix ion. However, it produces an interfering blank (e.g. sulfate for anion analysis with sulfuric acid as the regenerant). This is due to leakage of the acid regenerant used to supply the continuous source of hydronium ion for the neutralization reaction across the membrane.

Packed ion exchange resin bed columns have been used as pretreatment devices for the same purpose. Packed resin bed suppressors also have an interfering blank for subsequent ion analysis. Moreover, they lack adequate capacity.

A typical sample requiring analysis for trace anions is commercially available sodium hydroxide. The sample can be diluted to a concentration that is compatible with the column capacity, but the required sensitivity for the anions in the original solution is decreased to an unacceptable level due to dilution.

SUMMARY OF THE INVENTION

In accordance with the invention, apparatus and methods are provided for pretreating sample streams in a concentrated matrix compound causing neutralization of that compound to a substantially unionized form without the interference of blank contaminants introduced in prior art techniques. The pretreatment is particularly effective for subsequent analysis by ion chromatography.

The system includes pretreatment means in the form of an electrochemical membrane device in which sample flows through a sample flow channel of the device separated from a matrix ion receiving flow channel by an ion exchange membrane preferentially permeable to the same charge as the matrix ions and including exchangeable ions of that one charge. The pretreatment device includes electrodes in electrical communication with the sample flow channel and matrix ion receiving flow channel. The ionic species in the pretreatment sample device are directed to an analytical system comprising means for separating the ionic species and detector means for detecting the separated ionic species.

A preferred form of pretreatment means includes two ion exchange membranes defining the sample flow channel. A matrix ion receiving channel is on one side of one ion exchange membrane, and a water flow channel is on the opposite side of the membrane. The electrodes are in these outside flow channels.

In another preferred embodiment, the apparatus includes ionic species concentration means disposed downstream of, and in communication with, the pretreatment means for collecting and concentrating the ionic species to be detected. After concentration, the ionic species are eluted from the concentration means and directed to the analytical system.

In another preferred embodiment, for use with a sample for which the pretreatment device has insufficient capacity, conduit means is provided for recycling the liquid sample stream to the sample flow channel as many times as desired to accomplish pretreatment prior to flow to the analytical system.

In operation, the sample ionic species are pretreated in the electrochemical pretreatment means to remove matrix ions of opposite charge to the ionic species and replace them with hydroxide or hydronium ions causing neutralization of the matrix compound to a substantially unionized form. The sample stream flows through the sample flow channel of the pretreatment means separated by an ion exchange membrane from the matrix ion receiving flow channel in which a matrix ion receiving aqueous stream flows. The matrix ions are diffused through the ion exchange membrane into the matrix ion receiving channel while an electrical potential is passed between the sample flow channel and matrix ion receiving flow channel transverse to sample flow. Thereafter, the ionic species are passed, either in the same sample stream or after concentration to an analytic system including means for separating them, preferably a chromatography column. Thereafter, the separated ionic species are detected. In an ion chromatography system, a suppressor, suitably of the same type as the pretreatment means, is interposed between the chromatography column and detector, preferably an ion conductivity detector.

BRIEF DESCRIPTION OF THE DRAWINGS

FIG. 1 is a schematic block flow diagram of apparatus for performing chromatography using the electrochemical pretreatment system of the present invention.

FIG. 3 is a side view of an electrochemical pretreatment device according to the present invention illustrated inlet and outlet connectors.

FIG. 4 is a schematic expanded view of a two membrane electrochemical pretreatment device illustrating ionic transfer.

FIGS. 5 and 6 are an exploded view and assembled cross-sectional view, respectively, of an electrochemical pretreatment device illustrating a single membrane and device.

FIGS. 7 and 8 are schematic cross-sectional views of two different tubular forms of electrochemical pretreatment devices.

FIGS. 9a–f illustrate a sample pretreatment system according to the invention with valving in different sequential positions corresponding to the steps in the process.

FIGS. 10a and 10b are chromatograms illustrating the detection of trace anions in sodium hydroxide.

FIGS. 11a and 11b are chromatograms illustrating the detection of trace cations in sulfuric acid.

DETAILED DESCRIPTION OF THE PREFERRED EMBODIMENTS

Figure 2:
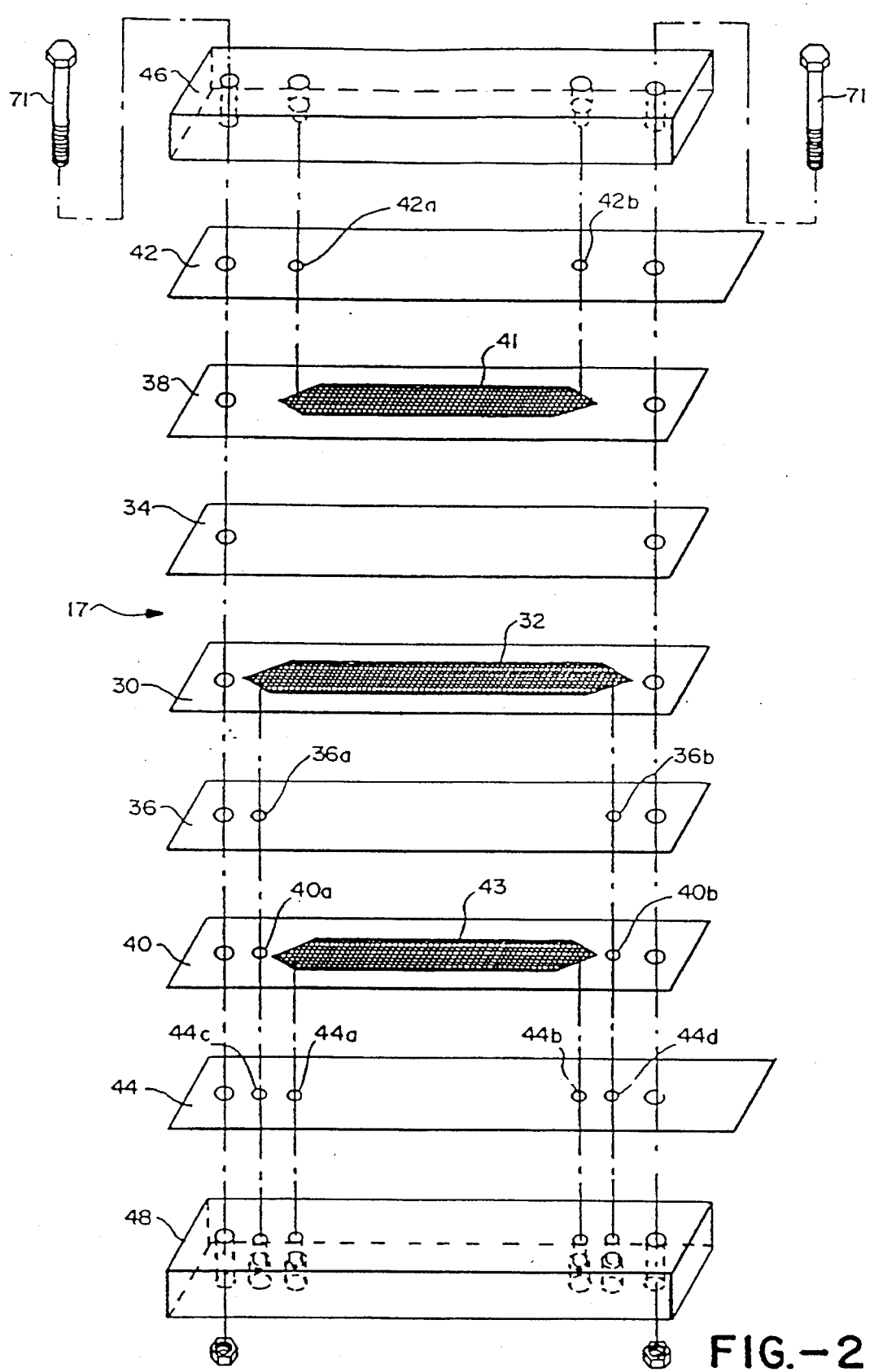
FIG. 2 is an exploded view of the electrochemical pretreatment device useful for a present invention.

The system of the present invention is useful for determining a large number of ionic species in a sample containing a matrix compound so long as the species to be determined are solely anions or solely cations. A suitable sample includes concentrated sodium hydroxide, for the determination of anions, or concentrated sulfuric acid, for the determination of cations.

When the term "ionic species" is used herein, it includes species in ionic form and components of molecules which are ionizable under the conditions of the present system.

As used herein the term "matrix compound" means an acid or base capable of being suppressed or neutralized by removal of the matrix ion of opposite charge to the acidic or basic species by diffusion through the ion exchange membrane of the pretreatment device. The diffused matrix ion is replaced by hydroxide or hydronium ion forming a substantially unionized compound, water.

For anion analysis, the matrix compound is a base (typically NaOH or other alkali metal hydroxides). Other possible matrix compounds include sodium carbonate, ammonium hydroxide, amines or tetra-alkyl ammonium hydroxides such as tetramethyl or tetrabutyl ammonium hydroxide. For cation analysis, the matrix compound is an acid, typically a common mineral or organic acid (e.g. sulfuric acid, phosphoric acid or methane sulfonic acid).

The pretreatment technique is used when the matrix ion is present at a sufficient concentration relative to the ionic species to be detected to interfere with separation, as by chromatography, or subsequent detection. A typical minimum concentration to warrant use of the system is when the matrix ion is present at least 10 times the molar ionic concentration of the chromatographic eluent.

Referring to FIG. 1, a schematic block flow diagram illustrating the pretreatment system of the present invention is illustrated in combination with an ion chromatography analytical system. In this instance, the analytical system includes a chromatographic separator column 10 which is packed with chromatographic separation medium. In one embodiment, such medium is in the form of ion-exchange resin. In another embodiment, the separation medium is a porous hydrophobic chromatographic resin with essentially no permanently attached ion-exchange sites. This other system is used for mobile phase ion chromatography (MPIC) as described in U.S. Pat. No. 4,265,634. An ion exchange site-forming compound, including hydrophobic portion and an ion-exchange site, is passed through the column and is reversibly adsorbed to the resin to create ion-exchange sites.

Arranged in series with column 10 is suppressor means 11 serving to suppress the conductivity of the electrolyte of the eluent from column 10 but not the conductivity of the separated ions.

The effluent from suppressor means 11 is directed to a detector, preferably in the form of flow-through conductivity cell 12, for detecting all the resolved ionic species therefrom. A suitable sample flows through a sample injection system 13 (including an electrochemical detection pretreatment device to be described). The sample flows through the system in the solution of eluent from eluent source or reservoir 14 drawn by pump 15. The chromatography effluent solution is passed through guard column 16, separation column 10, and then is directed to suppressor means 11 wherein the eluent electrolyte is converted to a weakly conducting form. The suppressed chromatography effluent with separated ionic species and passes through conductivity cell 12.

Sandwich Electrochemical Pretreatment Device

Referring to FIGS. 2–5, a pretreatment device is illustrated in the form of a sandwich suppressor device of the type illustrated in U.S. application Ser. No. 07/833,334. It includes a central sample flow channel defined on both sides by ion-exchange membranes to the exterior of which are a matrix ion receiving flow channel and a water flow channel, respectively. (The pretreatment device will be described prior to the description of the detailed flow diagram of FIG. 9.)

Referring specifically to FIGS. 2 and 3, electrochemical pretreatment device 17 is illustrated which includes a central sample flow channel flanked by two outside flow channels separated by ion exchange membranes. Device 17 includes means defining a sample flow channel in the form of a sample compartment, partially bounded by sample gasket 30 defining a central cavity. To minimize dead space in the cavity, it is preferable to form both ends of the flow channels in a peak or V-shape. Flow-through ion-exchange means, preferably bridging means in the form of sample screen 32, is disposed in the cavity. Membrane sheets 34 and 36 are mounted to extend along opposite sides of sample screen 32 and, together with gasket 30, define the outer perimeter of the sample flow channel. Openings 36a and 36b are provided for effluent inlet and outlet to the effluent flow channel.

Gaskets 38 and 40 are mounted to the facing surfaces of membrane sheets 34 and 36, respectively and define matrix ion receiving and flow channels. Bridging means may be provided in the flow channels in the form of screens 41 and 43, respectively. Openings 40a and 40b are provided for inlet and outlet flow through gasket 40. To simplify connections with the external flow lines, it is preferable to form the sample flow channel slightly longer than the flanking flow channels.

As illustrated, spaced electrode means in the form of flat plate electrodes 42 and 44, are placed on the exterior sides of gaskets 38 and 40, respectively, extending substantially across the length and width of the chambers in the gaskets. An electrical potential is applied across the electrode means. Electrode 42 includes openings 42a and 42b to permit the inlet and outlet flow of water to the detector effluent flow channel in gasket 38. Similarly, electrode 44 includes inlet and outlet openings 44a and 44b, respectively, for water flow to the water flow channel and gasket 40, and also defines inlet and outlet openings 44c and 44d for the chromatography effluent flow channel defined by gasket 30.

External support blocks 46 and 48 are formed of a rigid nonconductive material, such as polymethylmethacrylate, or polyether-ether ketone (PEEK) and serves to provide structural support for the remainder of membrane device 17. Referring to FIG. 3, fittings 50 and 52 are provided for detector effluent inlet and outlet lines 54 and 56, respectively. Similarly, fittings 58 and 60 are provided for water and matrix ion receiving inlet and outlet lines 62 and 64, respectively. Fittings 66 and 68 are provided for inlet and outlet lines 70 and 69, respectively. The fittings may be mounted to the support blocks by any conventional means such as mating screw threads.

The above assembled sheets and gaskets are mounted under pressure supplied by bolts 71 to form liquid-tight seals. Also, by use of such pressure in combination with appropriate sizing of the screen (or other bridging means described below) in comparison to the flow channel dimensions, the screen extends substantially the entire distance across the flow channels and contacts the membranes, resulting in significantly improved ion transport and efficiency.

Gasket 30 may be formed of any suitable material which provides a liquid seal for the chromatography effluent flow channel which it defines. A suitable material for the gasket is a flexible liquid silicone-based rubber such as supplied under the name RTV by General Electric Co. or a plastic sheet such as "Parafilm" supplied by American Can Co. A similar material may be used for detector effluent gaskets 38 and 40.

Ion-exchange membrane sheets 34 and 36 may be of a type such as disclosed in U.S. Pat. No. 4,486,312. In particular, such sheets may be cation-exchange or anion-exchange membranes with polyethylene, polypropylene, polyethylene-vinylacetate-based substrates. Other suitable substrates include polyvinylchloride or polyfluorocarbon-based materials. The substrate polymer is solvent and acid or base resistant. Such substrates are first grafted with suitable monomer for later functionalizing. Applicable monomers include styrene and alkylstyrenes such as 4-methylstyrene, vinylbenzylchloride or vinylsulfonates, vinylpyridine and alyklvinylpyridines. As an example, to form a cation-exchange membrane, the sheets grafted with styrene monomers are functionalized suitably with chlorosulfonic acid, sulfuric acid, or other $SO_2$ or $SO_3$ sources. To form an anion-exchange membrane, the sheets grafted with vinylbenzylchloride monomers are functionalized with alkyl tertiary amines such as trimethylamine or tertiary alkanolamines, such as dimethylethanolamine. Particularly effective membranes are no more than 10 mil thick, and preferably no more than 2–4 mil when wet. Suitable polyethylene substrate membranes of the foregoing type are provided by RAI Research Corp., Hauppauge, N.Y. (the cation exchange membrane provided under designation R5010 (0.008 in. thick) and the anion-exchange membrane under designation R4015 (0.004 in. thick)). Other cation exchange membranes supplied by the same company which are fluorocarbon based include R1010 (0.002 inch thick) and R4010 (0.004 inch thick).

Screen 32 may be formed integral with gasket 30 or may be inserted independently into the flow channel. A screen integral with the surrounding gasket material may be formed by cutting a gasket from plastic sheet to include the desired flow path and pressing this gasket into a rectangular piece of screen such that only the flow path is not covered by the gasketing material.

Screens 41 and 43 may be formed in the same manner as set forth with respect to screen 32.

Flow-through ion-exchange means, preferably in the form of bridging means, includes continuous portions which extend substantially the entire distance across the sample flow channel transverse to flow. In the embodiment of FIGS. 2 and 3, this distance extends between membrane sheets 34 and 36. In the alternate embodiment of FIG. 6 described below, only one membrane separates the sample flow channel from the membrane ion receiving flow channel. There, the transverse distance spanned by the bridging means is from the membrane to the opposite wall defining the sample flow channel. The bridging means defines a continuous convoluted flow-through passageway in the flow channel along substantially the entire length of the membrane. This creates turbulence and thus increasing the efficiency of mixing and transfer of the ions across the membrane as described below. The physical configuration of the screen may vary so long as its bridging function and turbulence-producing function is accomplished. Thus, the screen may be provided with a weaving pattern either perpendicular or diagonal to the direction of flow. Also, the fibers may be smooth or contain protrusions such as bumps.

A major function of the flow-through ion-exchange means is to provide a site-to-site path for ions in the direction transverse to the sample flow channel to increase the efficiency of ionic transfer across the ion-exchange membrane as more fully described below. Bridging means in the form of a screen may be functionalized for this purpose in a manner analogous to the functionalization of the ion-exchange membranes set forth above. Suitable screens may be formed of the same base polymers grafted with the same functionalizing monomers as those set out above for the membranes.

One preferred form of the screen embodiment of the flow-through ion-exchange means may be achieved using a relatively small mesh (measured after functionalization), e.g. on the order of 110 μ mesh size or less with relatively thin fibers, e.g., on the order of 0.004 inch in diameter.

Parameters relevant to the screen's function are set out in U.S. Pat. No. 4,999,098, incorporated herein by reference.

In the embodiments of FIGS. 2 and 3, an electrical potential from a direct current source (not shown) is applied between electrodes 42 and 44 from any suitable source. The electrodes are formed of highly conductive material which is inert to the solutions being passed through the membrane suppressor. Platinum is a preferred form of electrode for this purpose.

In one mode of operation of the pretreatment device 17, a liquid sample including matrix compound is directed through the sample flow channel bounded on both sides by ion-exchange membranes 34 and 36 partitioning the sample flow channel 45 from the matrix ion receiving flow channel 47 and water flow channel 49, respectively. (The valving arrangement for supplying such streams will be described with respect to FIG. 9.) The membranes are preferentially permeable to ions of the same charge as the exchangeable ions of the membrane and resists permeation of ions of opposite charge. The exchangeable ions of the membrane are in the ion form necessary to convert the matrix compound to a weakly ionized form. For maximum capacity, flow in channels 47 and 49 is countercurrent to the flow in channel 45.

The membranes are simultaneously contacted on their outer sides with the aqueous solutions flowing in the opposite direction so that the membranes form a selective permeability partition between the aqueous solutions and the sample stream. Matrix ions extracted from the sample at the active ion-exchange sites of the membrane partition with the matrix ion receiving flow channel are diffused through the membrane. Such matrix ions are exchanged for ions electrolytically generated in the water flow channel which pass through the bridging means, and through the other membrane into the sample flow channel. Application of a potential across the electrodes increases the mobility of the ions across the membrane, as well as electrolytically generating the ions required for neutralization of the sample.

It is not necessary to completely neutralize the matrix compound sample prior to introduction into the analytical system; it is only important to reduce the interference caused by the matrix acid or base concentration to a level that does not significantly interfere with subsequent concentration step or chromatography. Typically, reduction of such interference below 10 times the total molar ionic concentration of the eluent is sufficient.

FIG. 4 schematically illustrates the electrochemical operation of the present pretreatment device of the invention for a particular system, using a sandwich device with ion exchange screens in all flow channels, and applying an electrical potential between spaced electrodes. The system illustrated is for anion analysis and includes sodium hydroxide as the matrix compound to be converted into weakly ionized form (water). Thereafter, the solution passes to the detection system. The ion-exchange membrane sheets allow only the positively charged sodium and hydronium ions to permeate across the membranes together.

A suitable ion-exchange membrane for this purpose is a styrene-grafted, sulphonated, polytetrafluoroethylene or polyethylene sheet. Hydroxide ions tend not to permeate the membrane sheet because of Donnan Exclusion forces. Thus, the sodium hydroxide is converted to deionized water and the sodium ions of the NaOH matrix compound permeate the membrane sheet and are dispersed in the negatively-charged matrix ion receiving flow channel as NaOH which ultimately routed to waste. Applying a potential across electrodes 42 and 44 increases the kinetics of ion flow across the membrane and thereby increases capacity and, thus, the neutralization efficiency of the sample pretreatment device.

In the illustrated embodiment, the sodium ions of the electrolyte in sample channel 45 diffuse across the negatively-charged membrane into flow channel 47 under the influence of the negative electrode. The hydronium ions generated at the anode by electrolysis of water, flow from the positively-charged water flow channel 49 adjacent the positive electrode across membrane 36 into the sample flow channel to form water with hydroxide ions therein. The sodium ions, being attracted to the negative electrode, are more rapidly removed from the effluent channel leading to a substantial increase in the capacity of the membrane device.

In operation of the system of FIG. 4, in the positively charged water flow channel 49, hydronium ion is generated for passage through membrane 36 according to the following equation:

$$6H_2O \rightarrow 4H_3O^+ + O_2 + 4e^- \qquad (1)$$

In the sample flow channel, the sodium ion passes through membrane 34 under the influence of the cathode. Hydroxide is converted to water according the following equation:

$$OH^- + H_3O^+ \rightarrow 2H_2O \qquad (2)$$

In the negatively-charged sample matrix ion receiving flow channel, the sodium ion is converted to NaOH with hydroxide ion produced by the following equation:

$$4e^- + 4H_2O \rightarrow 4OH^- + 2H_2 \qquad (3)$$

A major advantage of using the above electrochemical pretreatment device, in contrast to a non-electrolytic membrane suppressor, is the elimination of a system blank (e.g. sulfate ion for anion analysis). To avoid interference from contaminants, it is preferable to use pure (e.g. 18 megohm-cm) water as the source of the aqueous solution flowing in the water flow channel and in the matrix ion receiving channel. However, such contaminants may be present in either solution so long as they do not interfere with analysis.

Ion Exchange Screens 32, 41 and 43 substantially increase the capacity of the pretreatment device to remove ions from the sample stream. The threads of the screen preferably extend substantially across the sample flow channel transverse to flow to contact both membranes. In the illustrated device, the sample screen extends the distance between membranes 34 and 36.

The functionalized screens include exchangeable ions of the same charge as those of the membranes. In this manner, the screen provides a direct site-to-site contact between the membrane walls for the ions to be diffused through the membranes. It has been found that the capacity of the system is significantly increased by the use of such functionalized screen in all flow channels.

Referring again to FIG. 3, any of the flow channels may include neutral screens rather than functionalized screens, although this system does not have as much capacity. The advantage of such unfunctionalized screens is that they provide turbulence in the detector effluent flow channel to increase the mixing efficiency. However, if desired, such screens may also be eliminated.

While the above sandwich pretreatment device includes a central sample flow channel separated by two membranes from two coextensive flow channels, the system is also applicable to the use of a single matrix ion receiving flow channel separated from the sample flow channel by a single membrane.

Referring to FIGS. 5 and 6, another embodiment of the pretreatment device 70 is illustrated using a single matrix ion receiving flow channel. Pretreatment device 70 includes upper rigid support block 72 with sample flow channel wall 73 and lower support block 74 with matrix ion receiving flow channel wall 75, separated by an ion-exchange membrane 76 of the type described above.

The sample flows into the pretreatment device through inlet 78, fitting 80 and flows along sample flow channel defined by wall 73, through screen 94 and then through fittings 82 and out sample outlet line 84. Similarly, water flows from inlet line 86 through fittings 88 across the matrix ion receiving flow channel defined by wall 75, out fitting 90 and through detector effluent outlet 92 to waste. The device of FIGS. 5 and 6 is used in the overall system of FIG. 1 in place of the device of FIGS. 2–5.

The liquid flows through the channels formed by the spacing among the projections. The dimensions of the projections and spacing is selected to provide the desired frequency of contacts with the flowing ions to increase their mobility across the membrane and to create sufficient turbulence for increased mixing efficiency.

Typically high concentration matrix compounds to be removed for analyzing anions by ion chromatography include alkali metal hydroxides, such as sodium hydroxide, and other bases (e.g. ammonium hydroxide, sodium carbonate and tetraalkyl ammonium hydroxide such as tetramethyl or tetrabutyl ammonium hydroxide). Suitably, the metal concentrations to be removed may vary from about 0.1 molar to 15 molar. If the matrix compound concentration in the sample stream is too high to be reduced to a sufficient extent during pretreatment, it may be diluted before pretreatment or recycled through the pretreatment device as described below.

The system of the present invention also is applicable to the analysis of cations (e.g., lithium, sodium, ammonium, potassium, magnesium, and calcium). In this instance, the matrix compound is typically a mineral acid such as sulfuric acid, so long as it does not damage the membrane. Other acids such as nitric acid and hydrochloric acid may be neutralized so long as the ion exchange membranes and screens are selected to be relatively inert.

To analyze cations, and thereby to neutralize acidic matrix compounds, the flow of the matrix ion is from the cathode toward the anode, rather than the reverse as in anion analysis and the ion exchange screens and membranes are aminated and permeable to anions. Thus, in the negatively charged flow channel 47, water is converted to hydroxide ion and hydrogen gas. The hydroxide ion passes through the adjacent membrane into the sample flow channel 45 and combines with hydrogen ion (or an amine or other basic organic molecule group) to form weakly ionized electrolyte. The negatively-charged matrix ion travels through the second membrane into the positively-charged matrix ion receiving flow channel 49 under influence of the anode to forman acid which passes to waste.

The above system illustrates an ion exchange screen as the preferred flow-through ion exchange means. However, it should be understood that other ion exchange means may also be employed for the sandwich pretreatment device or other relatively flat pretreatment device. For example, ion exchange particles may be packed in the flow channels for this purpose. Here, it would be preferable to include some mode to keep the ion exchange particles in the device by using a porous polymeric support that has smaller pores than the resin being used, such as sintered polyethylene available from General Polymeric.

Referring to FIG. 7, a schematic cross-sectional view of a tubular form of the electrochemical pretreatment device of the present invention is illustrated. In this instance, it is assumed that the sample channel is the lumen of the innermost tube. The device includes anode 122 (in the form of a rod or wire, e.g., formed of platinum, gold, carbon or stainless steel), cation exchange membrane 124, and outer wall 126, which may be formed of a conductive material to serve as the cathode. Preferably, flow-through ion exchange means in the form of ion exchange resin is disposed in the chromatographic effluent flow channel, the detector effluent flow channel or both. This system is comparable in general function to the one illustrated in FIG. 4. Alternatively, the matrix ion receiving flow channel may be the lumen of the inner tube. In this instance, the polarities of the electrodes are reversed. Membrane 124 may be formed of stretched or unstretched tubular ion exchange membranes, e.g., Nafion 811X from Perma-Pure Products, N.J. Outer wall 126 may be formed of an 18 GA. stainless steel (SS) tubular case.

FIG. 8 illustrates a tubular type or dual-membrane pretreatment device of similar function to the sandwich pretreatment device. It is generally constructed by inserting a length of suitably inert wire inner electrode 128 into a length of tubular inner membrane 130 which is itself inserted inside a length of somewhat larger diameter tubular outer membrane 132 and enclosing the whole assembly in the stainless steel tube 134 of appropriate dimensions. The outer tube itself functions as the electrode, connections being made at the ends to allow access to the flow channels between the inner electrode and inner membrane, between the two membranes (annulus) and between the outer membrane and stainless steel case.

The power requirements for this system are dependent to some extent upon the flow rate through the system and the concentration of matrix compound. For this purpose, a suitable flow rate sample solution are about 0.01 to 10 mls/min. and, preferably, 0.25 to 2 mls/min. For such flow rates, suitable power requirements are 2 to 20 V (preferably 3 V to 5 V) with a current between 0.010 A and 2.0 A (preferably about 0.30 A to 1.0 A). This applies to both the flat membrane and tubular membrane assemblies.

Other alternative configurations (not shown) of the pretreatment device can be used in accordance with the present invention. For example, referring to the device of FIGS. 2–4, the positions of screens 41 and 43 may be reversed with the positions of electrodes 42 and 44, respectively. Specifically, in such alternative configurations, electrodes 42 and 44 extend along, and are pressed flush against, ion exchange membranes 34 and 36, respectively. The electrodes are in contact with the solution flowing through the outside flow channels. In this instance, the electrodes include openings to permit ion transport across the ion exchange membranes between the outside flow channels and the central sample flow channel. Such openings may be formed in a number of known ways, e.g., by punching of spaced holes (typically from 0.010" to 0.250" across), or by forming the electrodes of a woven screen, or by notching an inert foil electrode so that the electrode forms a zig-zag or serpentine pattern along the length of the chamber. For example, platinum wire bent into a zig-zag pattern can be used, however, solid platinum or platinum plated foil is preferable to prevent excessive resistive heating.

In another embodiment (not shown), a "hybrid" pretreatment device may be formed in which the electrode and screen is in the configuration illustrated in FIGS. 2–4 for one of the outside flow channels while in the opposite outside flow channel the electrode and screen are reversed in the manner described in the previous paragraph. An effective hybrid configuration for an ion analysis is formed in which an anode with spaced openings is flush against the ion exchange membrane and the cathode (the compartment to the left of FIG. 3) is in the configuration illustrated in FIGS. 2–4. The same configuration is preferred for cation analysis.

The above pretreatment system is described in combination with an ion chromatography analytical system. However, the pretreatment system is also compatible with other detection equipment and methods capable of detection the ions of interest in the sample matrix. For example, the pretreatment system can be used with an ultraviolet (UV) or visible detection indirect UV or visible detection, amperometric detection, none of which require the use of a suppressor.

To determine if the sample has been sufficiently treated in the pretreatment device, a conductivity cell may be placed at the outlet of the device to monitor sample conductivity. When the sample matrix compound concentration has been reduced to an acceptable level, the sample slug is directed to the collection loop.

In the illustrated system, the concentrated sample is first loaded into a loading loop and then driven through the pretreatment device by a stream of water using a mechanical pump. Since the pretreatment device has only been exposed to water prior to the introduction of the sample slug, it is fully charged and thus has a higher capacity for neutralization in comparison to continuously neutralizing a sample stream. In an alternative embodiment, if the capacity of the pretreatment device is sufficient to accommodate the matrix compound concentration continuously, an injection loop may be dispensed with and the pretreatment sample stream may be fed continuously on-line to the pretreatment device.

If the matrix compound concentration in the sample is too high for the pretreatment device, with an appropriate set of valving, it is possible to recycle the injected sample volume through the sample preparation device a number of times to reduce its concentration to that compatible with the downstream analytical (typically chromatographic) system. In this system, the sample is loaded into a sample loading loop as illustrated in FIGS. 9a–f and passed through the sample pretreatment device. Then, it is redirected or recycled through the device until the sample concentration is reduced to an acceptable level. To determine this, a conductivity cell can be placed at the outlet of the device to monitor sample conductivity. When the sample matrix concentration has been reduced to an acceptable level, the sample slug is directed to the collection loop. In this instance, the collection loop is sufficiently larger than the sample loading loop to account for the dispersion in the sample passing through the device. For example, if the sample loading loop is 10 μL to 50 μl, the collection loop can be on the order of 3 mL. The sample slug is then directed to a concentrator column to reconcentrate the diluted ionic species of interest prior to injection in the analytical system. Using this system, it is possible to analyze anions in a concentrated matrix (e.g. 50% w/w sodium hydroxide), with no dilution of the sample required for analysis.

In another alternative, if the concentration of ions to be determined is below the detection limit by loop injection and the major matrix ion is at a concentration where it can be continuously removed by the sample treatment system a concentrator column can be used in place of the mechanical pump through the sample preparation system and the neutralized sample stream is passed across the concentrator column. After a known volume (e.g. 2 to 50 mL), of the neutralized sample (determined by for example monitoring the flow rate of sample stream) has been passed across the concentrator column, the injection valve to which the concentrator column is connected is actuated, placing the concentrator column in the analytical stream where the analytes of interest are separated and detected.

Referring to FIGS. 9a–f, a system is illustrated including appropriate valve settings for sequential steps, using the pretreatment device of the present invention in combination with a conventional sample loop end with a collecting coil and a concentrator column downstream of the pretreatment device.

FIG. 9a illustrates the valve setting for sample introduction. Sample is directed by an automatic sample introduction device 150 through four-way valve 156 into sample injection loop 154, through four-way valve 152 and to waste illustrated by arrow 158. The sample loop, typically in the form of coiled polymer tubing, stores a predetermined amount of sample to be analyzed. The capacity of the sample loop may vary depending upon the system. A suitable capacity for a typical sample is on the order of 0.01 ml to 0.5 ml, and more typically 0.05 ml to 0.2 ml.

Referring to FIG. 9b, the first stage of sample pretreatment is illustrated. In this instance, pump 160, suitably a single piston pump, is activated to drive high purity water from a source, not shown, through valve 152 in its other position, as illustrated, through sample loop 154, valve 156, also in its other position, four-way valve 162, recycle loop 164, four-way valve 166 and into electrolyte sample pretreatment device 168 of the type described above. From there, the sample is directed through a suitable detector, conductivity cell 170, back through valve 162 and through second recycle loop 174, valve 166, four-way valves 176 and 184 and to waste as illustrated by arrow 180. The recycle loops 164 and 174, suitably polymeric coiled tubing sections, are used to store sample during the pretreatment cycle. They typically have a volume of 3.0 ml to 5.0 ml.

If the sample contains relatively low concentration of matrix ions so that a single pass through pretreatment device 168 is sufficient, recycle loops 164 and 174 serve no function. Then, as illustrated in FIG. 9d, the sample is only directed once through sample pretreatment device 168 to collection loop 182.

If the sample contains high concentration of matrix ions (e.g. 25% sodium hydroxide or 48% sulfuric acid), multiple cycles through pretreatment device 168 are used, as illustrated in FIG. 9c. The need for this additional step in the overall process can be monitored by conductivity cell 170.

Referring to FIG. 9c, the position of valves 162 and 168 are reversed. Sample from valve 162 is directed through recycle loop 174, sample pretreatment device 168, conductivity cell 170, recycle loop 164, valve 166, valve 176, and to waste 180. High purity water delivered by pump 160 flushes the sample from recycle loop 164 back to pretreatment device 168. Then the sample band is collected in recycle loop 174. By combining the steps of FIGS. 9b and 9c, the sample is cycled twice through pretreatment device 168.

If a third recycle is required, the valve setting is changed to that shown in FIG. 9d for third cycle before collection in collection loop 182.

Referring to FIG. 9d, the sample is transferred to collecting coil 182. Here, immediately after the steps of FIGS. 9b or 9c, depending on the number of cycles, the valves are set as in FIG. 9d for recovery of the treated sample located in one of the recycle loops or 174. High purity water delivered from pump 160 flushes the sample from the selected recycle loop out to valve 168 and into collecting coil 182. Collecting coil 182 typically is a coiled polymer tubing section with a capacity of 5.0 to 10.0 ml in a loop. Collecting coil 182 serves to separate the low pressure pretreatment device 168 from the high pressure concentrator column 186 described hereinafter. After the sample is completely transferred from the recycle loops to collection coil 182, the valves are again changed as illustrated in FIG. 9e.

Referring to FIG. 9e, the sample is transferred from the collection coil 182 to concentrator means suitably in the form of an ion exchange concentrator column 186. Typical capacity is from 2.0 to 100 microequivalents per column, preferably 5–50 microequivalents per column.

Pump 186 (typically a single piston pump) is activated to deliver high purity water from a source, not shown, to flush the sample from collecting loop 182 through valve 176, valve 181, into concentrator column 186, through valve 188 to waste illustrated by arrow 190. At the end of this step, the ionic species in the treatment sample are collected in a tight band on concentrator column 186.

In the stage of the pretreatment system illustrated in FIG. 9e, the sample on concentrator column 186 is ready to be transferred to the desired separation and detection system.

Referring to FIG. 9f, the pretreatment device of the present invention is illustrated for use with an ion chromatography system. However, other separator systems could be employed by combining separation and detection. Separating eluent from a source, not shown, is pumped via pump 192 (suitably a standard analytical pump) through valve 188, concentrator column 186, valve 181 to the analytical system. As illustrated, the system comprises a separator column 194 (e.g. a chromatographic column sold by Dionex Corporation under the designation IonPac AS4ASC (Dionex PN43126)) through an eluent suppressor device 196. From there, the effluent is detected by conductivity cell 198 using data processor 200. A suitable analytical system of this general type is illustrated in U.S. Pat. No. 4,999,098.

It is apparent that the original liquid sample stream passing to the pretreatment device may be the same as the sample supplied for analysis or may be significantly different. For example, if the ions of interest are concentrated on a concentrator column prior to being directed to the pretreatment device, the liquid carrier stream for the ionic species is the eluent which removes such ionic species from the concentrator column. Thus, as used herein, the term "liquid sample stream" encompasses any stream directed to the pretreatment device that includes the ionic species to be detected and the matrix compound which is to be neutralized to a sufficient extent to prevent interference during subsequent analysis. Similarly, the term "pretreated sample stream" which is directed to the analytical system encompasses both the effluent from the pretreatment device and any liquid stream derived from that effluent. For example, such pretreated sample stream encompasses ionic species eluted from a concentration device downstream from the pretreatment device.

In another embodiment to that of FIGS. 9a–f, the system can be utilized without a collecting coil and concentrator column. Elimination of the collection coil and concentrator column is useful when the analytes of interest are detectable using loop injection. In this case the sample stream is passed through the sample preparation device manually or with a mechanical pump, through an injection loop, typically 0.010 to 0.250 μL. When the loop is filled with treated sample, the injection valve to which the loop is connected is actuated and the sample is injected into the analytical (typically chromatography) stream.

In order to illustrate the present invention, the following examples of its practice are illustrated.

EXAMPLE 1

In this example, trace anions in concentrated sodium hydroxide were determined. A 48% sodium hydroxide sample was run on the system of FIGS. 9a–9f using three cycles through pretreatment device 168, with and without spiking with trace anions. The spiked anions and concentrators were as follows:

| Anions | Concentration (ppm) |
| --- | --- |
| 1. chloride | 0.6 |
| 2. nitrite | 2.0 |
| 3. bromide | 3.0 |
| 4. nitrate | 3.0 |
| 5. phosphate | 3.0 |
| 6. sulfate | 3.0 |

The following conditions and components were used:

| Conditions | |
| --- | --- |
| Sample: | 48% (W/W) NaOH |
| Sample size: | 50 microliter |
| Recycle loop: | 3.0 mL |
| Eluent: | 1.8 mM Sodium carbonate |
| | 1.7 mM Sodium bicarbonate |
| Eluent Flow rate: | 0.5 mL/min |
| Pump 160 Flow rate: | 1.0 mL/min |
| Pump 186 Flow rate: | 1.0 mL/min |
| Pump 192 Flow rate: | 0.5 mL/min |
| Components | |
| Recycle Loops: | 3.0 mL |
| Anion Pretreatment Device 168: | ASRS (P/N 43189) |
| Collecting Coil 182: | 8.0 mL |
| Concentrator Column 186: | IonPac AC10 (Dionex P/N 43134) |
| Separator Column 194: | IonPac AS4ASC |
| | (Dionex P/N 43126) |
| Conductivity Cells: | CDM (P/N 04157) |
| Suppressor 196: | AMMS (P/N 43106) |

The analysis of the sodium hydroxide sample without spiking is illustrated in the chromatogram of FIG. 10a and with spiking in the chromatogram of FIG. 10b. The anion numbers in the above table correspond to the peak number designations on the chromatogram.

EXAMPLE 2

In this example, trace cations in concentrated sulfuric acid were determined. A 48% sulfuric acid sample was run on the system of FIGS. 9a–9f using three cycles through pretreatment device 168, with and without spiking with trace cations. The spiked cations and concentrators are as follows:

| Cations | Concentration (PPM) |
|---|---|
| Li | 0.5 |
| Na | 2.0 |
| NH$_4$ | 4.0 |
| K | 2.0 |
| Mg | 2.0 |
| Ca | 10.0 |

The following conditions and components were used:

| Conditions | |
|---|---|
| Sample: | 48% (W/W) sulfuric acid |
| Sample size: | 50 microliter |
| Eluent: | 22 mM Methansulfonic acid |
| Eluent Flow rate: | 1.0 mL/min |
| Pump 160: | 1.0 mL/min |
| Pump 186: | 2.0 mL/min |
| Pump 192: | 1.0 mL/min |
| Components | |
| Recycle Loops: | 3.0 mL |
| Cation Pretreatment Device 168: | CSRS (P/N 43190) |
| Collecting Coil 182: | 8.0 mL |
| Concentrator Column 186: | (1) MetPac CC-1 (Dionex P/N 42156) (2) TCC-1 (Dionex P/N 43103) |
| Separation Column 194: | IonPac CS 12 (Dionex P/N 44001) |
| Conductivity Cells: | CDM (P/N 40157) |
| Suppressor 196: | CMMS (P/N 43021) |

The analysis of the sulfuric acid sample without spiking is illustrated in the chromatogram of FIG. 11a and with spiking in the chromatogram of FIG. 11b.

What is claimed is:

1. An analytical method for analyzing ions in acid or base samples comprising (a) pretreating a liquid sample stream, comprising a plurality of ionic species to be detected and at least one matrix compound, by flowing said sample stream through electrochemical pretreatment means for removing at least part of the matrix ions of said matrix compound, said matrix ions being of opposite charge to said ionic species, and replacing said matrix ions with hydroxide or hydronium ions causing the neutralization of the matrix compound to a substantially unionized compound, said sample stream flowing through a sample flow channel of said pretreatment means in which said sample flow channel is separated by at least one ion exchange membrane from at least one matrix ion receiving flow channel, (b) flowing a matrix ion receiving aqueous stream through said one matrix ion receiving flow channel so that matrix ions from the sample flow channel are diffused through said one ion exchange membrane into said matrix ion receiving channel, (c) passing an electrical potential between said sample flow channel and said matrix ion receiving flow channel transverse to flow of said sample stream through said sample flow channel to assist diffusion of said matrix ions through said one ion exchange membrane, said matrix ion receiving channel being of opposite charge to said matrix ions, (d) recycling said pretreatment sample stream through said one matrix ion receiving channel, (e) separating the ionic species in said pretreatment sample stream, and (f) detecting said separated ionic species, wherein the pretreatment of steps (a) to (d) is capable of reducing a concentration of said matrix ions which would be otherwise incompatible with a downstream analytical system to a concentration that would be compatible with said downstream analytical system.

2. The method of claim 1 in which flow-through ion exchange means is disposed in said sample flow channel, said ion exchange means having ion exchange sites with exchangeable ions of the same charge as the exchangeable ions of said ion exchange membrane.

3. The method of claim 1 in which flow-through ion exchange means is disposed in said matrix ion receiving flow channel, said ion exchange means having ion exchange sites with exchangeable ions of the same charge as the exchangeable ions of said one ion exchange membrane.

4. The method of claim 1 in which the ionic species are anions and in step (c) water in said sample flow channel is electrolyzed to generate hydronium ions.

5. The method of claim 1 in which the ionic species are cations and in step (c) water in said sample flow channel is electrolyzed to generate hydroxide ions.

6. The method of claim 5 in which said sample flow channel is separated by a second ion exchange membrane, with exchangeable ions of the same charge as said matrix ions, from a water flow channel, whereby said one and second ion exchange membranes define said sample flow channel, said method further comprising directing water through said water flow channel, and in which said electrical potential is passed between said water flow channel and said matrix ion receiving flow channel through said sample flow channel to electrolyze water in said flow channel to assist diffusion of said matrix ions through said first ion exchange membrane by generating hydronium ions for anion analysis or hydroxide ions for cation analysis.

7. The method of claim 1 further comprising, between steps (c) and (d), (f) passing such pretreated sample stream to concentration means in which said ionic species are collected and retained, and (g) passing an eluent through said concentration means under conditions to elute said ionic species which are passed to separation means for performing the separation of step (d).

8. The method of claim 1 in which the separation of step (d) is performed chromatographically.

9. The method of claim 1 in which said matrix ion receiving aqueous stream entering said matrix ion receiving flow channel consists essentially of water.

* * * * *